(12) United States Patent
Bensberg et al.

(10) Patent No.: US 12,216,582 B1
(45) Date of Patent: Feb. 4, 2025

(54) DISK-BASED MERGE FOR COMBINING MERGED HASH MAPS

(71) Applicant: SAP SE, Walldorf (DE)

(72) Inventors: Christian Bensberg, Heidelberg (DE); Frederik Transier, Bammental (DE); Kai Stammerjohann, Wiesloch (DE)

(73) Assignee: SAP SE, Walldorf (DE)

( * ) Notice: Subject to any disclaimer, the term of this patent is extended or adjusted under 35 U.S.C. 154(b) by 0 days.

(21) Appl. No.: 18/228,193

(22) Filed: Jul. 31, 2023

(51) Int. Cl.
| | |
|---|---|
| *G06F 12/08* | (2016.01) |
| *G06F 12/0864* | (2016.01) |
| *G06F 12/0873* | (2016.01) |

(52) U.S. Cl.
CPC ...... *G06F 12/0864* (2013.01); *G06F 12/0873* (2013.01)

(58) Field of Classification Search
CPC ... G06F 12/08; G06F 12/0864; G06F 12/0873
See application file for complete search history.

(56) References Cited

U.S. PATENT DOCUMENTS

| | | | | |
|---|---|---|---|---|
| 8,352,494 | B1 | 1/2013 | Badoiu | |
| 10,248,677 | B1 * | 4/2019 | Visvanathan | ....... G06F 16/1748 |
| 11,528,322 | B1 * | 12/2022 | Chaudhary | ......... H04L 67/1014 |
| 2012/0011108 | A1 * | 1/2012 | Bensberg | ............ G06F 16/2255 |
| | | | | 707/E17.017 |
| 2017/0228373 | A1 * | 8/2017 | Mueller | ............... G06F 16/2255 |
| 2017/0286313 | A1 * | 10/2017 | Jiang | .................... G06F 12/0864 |
| 2019/0073152 | A1 | 3/2019 | Nagle et al. | |
| 2021/0089683 | A1 * | 3/2021 | Hemlin Billstrom | ........................ H04L 9/3239 |
| 2022/0292093 | A1 * | 9/2022 | Pishe | .................. G06F 16/2246 |
| 2023/0350810 | A1 * | 11/2023 | Thoppil | .............. G06F 12/1018 |

FOREIGN PATENT DOCUMENTS

| | | | | |
|---|---|---|---|---|
| EP | 2469424 | A1 * | 6/2012 | ......... G06F 16/2255 |
| GB | 2606526 | A * | 11/2022 | ............. G06F 21/64 |
| WO | WO-2010096750 | A2 * | 8/2010 | ......... G06F 17/3033 |

(Continued)

OTHER PUBLICATIONS

A. N. Gowda, A. M and N. Guruprasad, "Comparative Study of Hashing and Analysis of Collision Resolution Techniques," 2023 International Conference on IoT, Communication and Automation Technology (ICICAT), Gorakhpur, India, 2023, pp. 1-4.*

(Continued)

*Primary Examiner* — Pierre Michel Bataille
(74) *Attorney, Agent, or Firm* — Sterne, Kessler, Goldstein & Fox P.L.L.C.

(57) ABSTRACT

Various embodiments for a disk-based merge for combining merged hash maps are described herein. An embodiment operates by identifying a first hash map and a second hash map, and comparing a first hash value from the first hash map with a second hash value from the second hash map, with the lowest index values. A lowest hash value is identified based on the comparison, and an entry corresponding to the lowest hash value is stored in a combined hash map. This process is repeated until all of the hash values from both the first set of hash values and the second set of hash values are stored in the combined hash map. A query is received, and processed based on the combined hash map.

20 Claims, 16 Drawing Sheets

(56) References Cited

FOREIGN PATENT DOCUMENTS

| | | | |
|---|---|---|---|
| WO | WO-2014015828 A1 * | 1/2014 | ......... G06F 12/0806 |
| WO | WO-2019147441 A1 * | 8/2019 | ............. G06F 16/00 |

OTHER PUBLICATIONS

G. Meliolla, K. A. Nugroho and F. I. Hariadi, "Implementation of hash function on embedded-system platform using chaotic tent map algorithm," 2016 International Symposium on Electronics and Smart Devices (ISESD), Bandung, Indonesia, 2016, pp. 179-183.*

* cited by examiner

DISK-BASED MERGE FOR COMBINING MERGED HASH MAPS

CROSS-REFERENCE TO RELATED APPLICATIONS

This application is related to U.S. patent application Ser. No. 18/228,187, titled "Disk-Based Merge for Hash Maps", filed Jul. 21, 2023, which is herein incorporated by reference in its entirety.

BACKGROUND

Hash maps are often used when performing queries, to help identify various values. When there is a large amount of data to be stored and referenced or queried, a system may create multiple hash maps. However, maintaining and using multiple hash maps can consume greater storage space and processing capacity while also reducing the speed, throughput, and other computing gains that may have been achieved by using a hash map in the first place.

BRIEF DESCRIPTION OF THE FIGURES

The accompanying drawings are incorporated herein and form a part of the specification.

In the drawings, like reference numbers generally indicate identical or similar elements. Additionally, generally, the left-most digit(s) of a reference number identifies the drawing in which the reference number first appears.

DETAILED DESCRIPTION

Hash maps are often used when performing queries, to help identify various values. When there is a large amount of data to be stored and referenced or queried, a system may create multiple hash maps. However, maintaining and using multiple hash maps can consume greater storage space and processing capacity while also reducing the speed, throughput, and other computing gains that may have been achieved by using a hash map in the first place.

Figure 1:
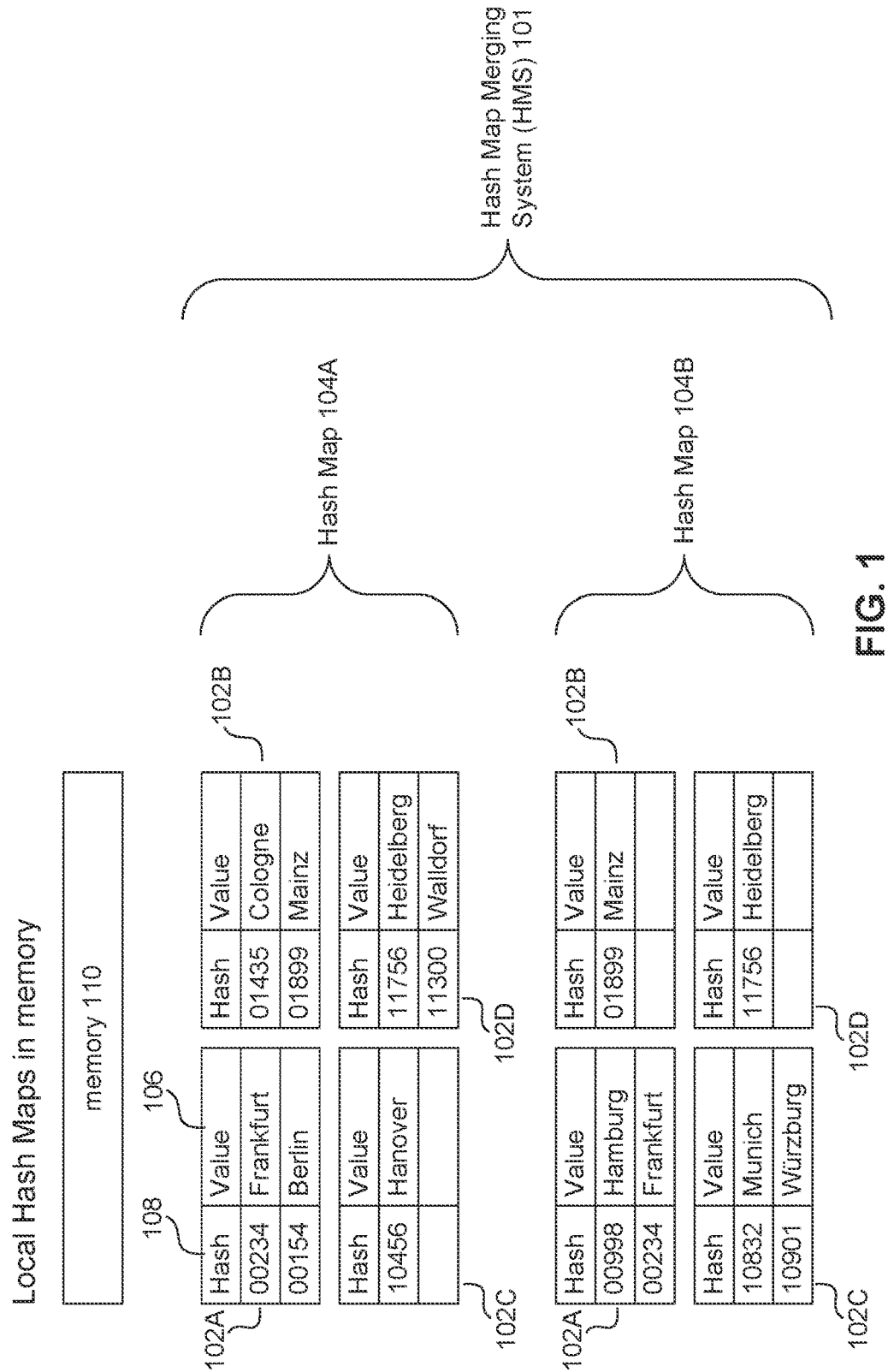
FIG. 1 illustrates an initial state of a hash map merging system (HMS) for performing a disk-based merge with hash maps, according to some embodiments.
Figure 4:
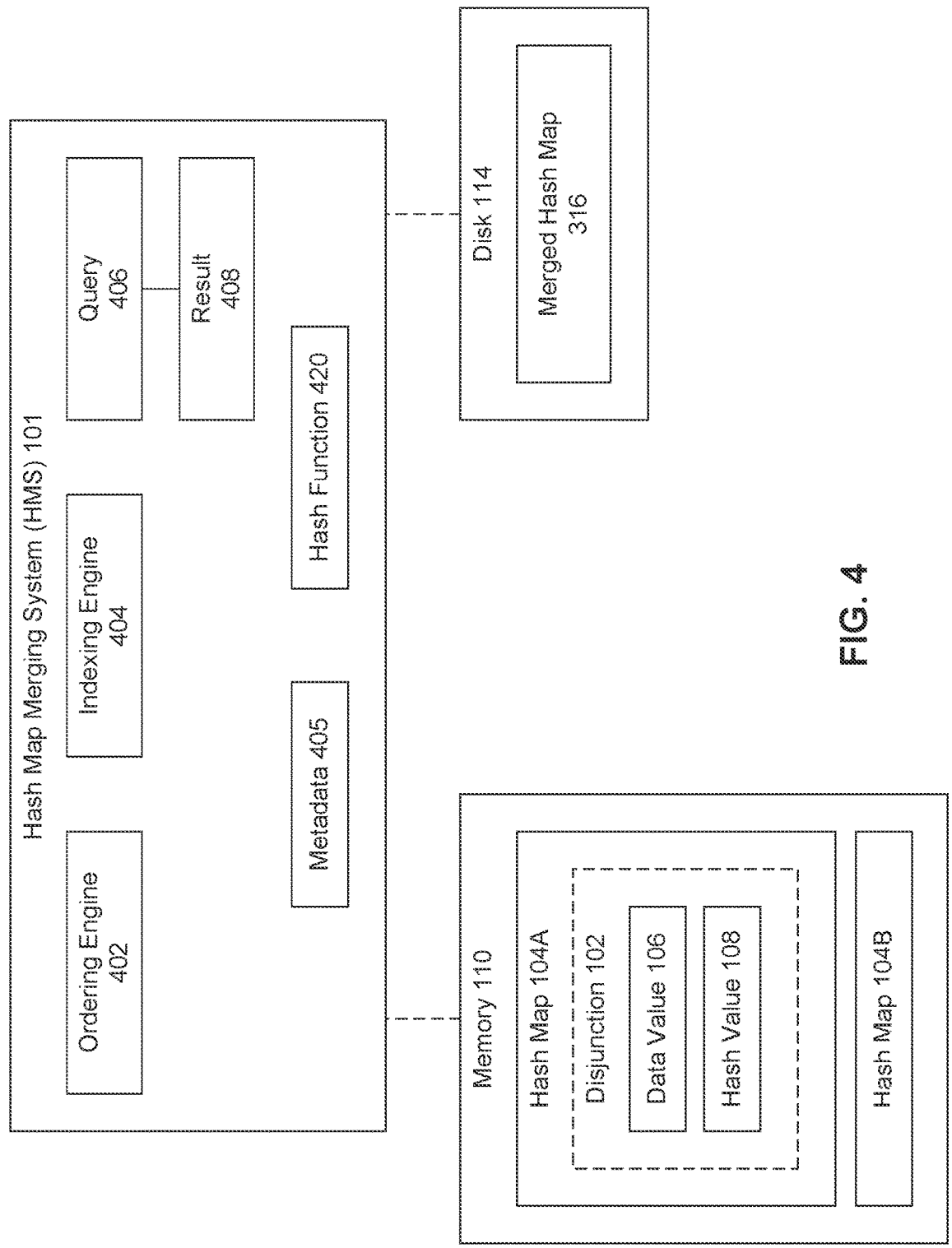
FIG. 4 is a block diagram illustrating a hash map merging system (HMS), according to some example embodiments.

FIG. 1 illustrates an initial state 100 of a hash map merging system (HMS) 101 for performing a disk-based merge with hash maps, according to some embodiments. Another example of HMS 101, with greater details, is illustrated in FIG. 4 and described in further detail below. HMS 101 may generate, merge, update, and combine hash maps 104A, 104B in ways that are memory efficient. Further the resultant hash maps may then be used by HMS 101 or another disk storage system for faster lookups during query processing. The hash map(s) generated by HMS 101 may help improve the lookup time when a computing system is performing queries, thus improving the query speed and overall system throughput of the system.

FIG. 1 illustrates two example hash maps 104A and 104B stored in a memory 110. The hash maps 104A, 104B (referred to herein generally as hash map 104, or hash maps 104) may be divided into or include a number of different portions or disjunctions 102A-D (referred to herein generally as disjunction 102 or disjunctions 102). In the example illustrated, each hash map 104 includes four disjunctions 102A-D.

In some embodiments, a hash map 104 may be generated or written to by multiple processors or threads of HMS 101 or another computing system or data storage system. Each thread may include a set of resources that is assigned or configured to write a set of disjunctive values to a specific one of the disjunctions 102 of a hash map 104. This thread assignment or set of disjunctive values to a particular disjunction 102 may help ensure that a particular data value 106 will occur or be written to the same disjunction 102, even if it occurs in different hash maps 104. In some embodiments, each disjunction 102 may be assigned to a particular range of hash values 108, such that all hash values 108 within that range are written to a particular disjunction 102. In some embodiments, HMS 1010 may use the most-significant bits of the hash value 108. When using the first two most-significant bits, there are four possible values (00, 01, 10 and 11), hence resulting in four disjunctions 102. For illustrative purposes, throughout all examples in this application, the first two digits (not bits) of the hash values 108 are either 00, 01, 10 or 11 to make it easy to relate them to their corresponding disjunction 102.

Using multiple threads to write to different disjunctions 102 may allow for a hash map 104 to be more rapidly generated, especially if there is a large number of data values to be included in the hash map. The use of disjunctions 102 may also allow multiple hash maps 104 to be created in parallel by multiple different computers or computing systems. In some embodiments, each thread may be responsible for writing to a hash map 104. Once the local hash maps are created, for further processing of the data, individual threads may work on specific disjunctions 102. For example, thread 1 may be responsible for processing data of disjunction 102A, while thread 2 may be responsible for processing disjunction 102B, and so on. In the given example, the value for the city Frankfurt is always in disjunction 102A and hence will then be processed by the same thread. This way, less locking is required than in other approaches.

As illustrated, HMS 101 or another computing system may have created multiple hash maps 104A, 104B. As just described, each disjunction 102A-D, of each hash map 104A, 104B, may include the same set of disjunctive values. For example, "Frankfurt" as illustrated in disjunction 102A of hash map 104A, can also be seen in disjunction 102A of hash map 104B. Frankfurt would not be found in a different disjunction (e.g., any of disjunctions 102B-D) of any other hash map 104. For simplicity only two hash maps 104 and four disjunctions 102 are illustrated, however it is understood other embodiments may include any multiple number of hash maps 104 and disjunctions 102 may be used.

In some embodiments, each disjunction 102 may include a data value 106 and a corresponding hash value 108. The hash value 108 may be a value generated by providing the data value 106 into a hash algorithm or hash function 420 (as illustrated in FIG. 4). By using the hash function 420, a data value 108 such as "Frankfurt" will generate an identical corresponding hash value 108 each time is it provided to the hash function 420, across the same or different hash maps 104. For example, Frankfurt has an identical hash value 00234 (as generated by hash function 420) in disjunction 102A of both hash map 104A and 104B.

In some embodiments, each hash value 108 may include a prefix identifying or corresponding to the disjunction 102 to which the hash value belongs or was retrieved. For example, each hash value in disjunction 102A begins with the prefix 00, each hash value in the disjunction 102B includes a prefix 01, each hash value in the disjunction 102C includes a prefix 10, and each hash value in the disjunction 102D includes a prefix 11.

As described above, in some embodiments, the prefixes may be binary bits (which may be value 0 or 1), rather than numerical integer values. Using bits may be more memory efficient than integer values. In other embodiments, integer values may be appended to the hash value as a prefix or postfix. In other embodiments, values other than 0-3 (00, 01, 10, 11) may be used, particularly if non-bit values are being used. For example, the values corresponding to the disjunction 102 may be stored in a different column or location (e.g., as part of metadata).

Figure 2:
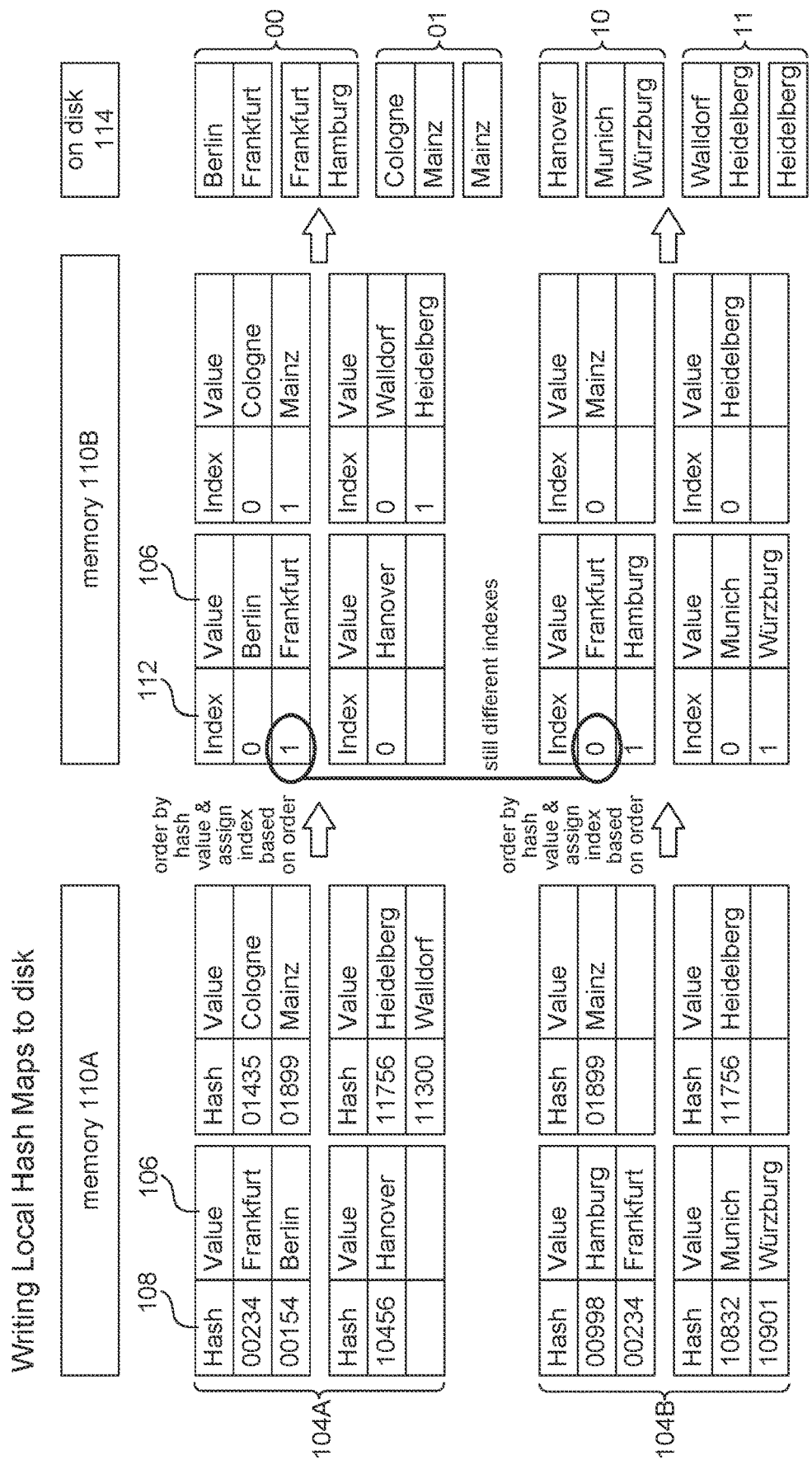
FIG. 2 illustrates example operations directed to performing a disk-based merge with hash maps in which data values are moved from memory to a disk location, according to some embodiments.

FIG. 2 illustrates example operations 200 directed to performing a disk-based merge with hash maps in which data values are moved from memory to a disk location, according to some embodiments.

In the example of FIG. 2, memory 110 is illustrated as memory 110A (initial state of what is stored in memory 110) and memory 110B (updated state of what is stored in memory 110)—but may be the same memory 110. The left side of FIG. 2 illustrates an initial system state 100 as described above with respect to FIG. 1.

In this initial system state, the hash maps 104A, B and their disjunctions 102A-D are stored in memory 110A of one or more computing systems or devices. In some embodiments, as part of the merging process, the values from the hash maps 104A, 104B may be moved to disk. For example, in some embodiments, there may be too many values in the hash maps 104A, 104B to perform the merging in memory 441 alone (e.g., because the merging process would consume too much memory, that would slow down other system processes or prevent them from executing efficiently or properly, or there may simply not be enough memory available to perform the merging process).

In some embodiments, HMS 101 may sort or order the entries in each disjunction 102 by hash value 108. For example, as illustrated in memory 1101B, the order of the values (Berlin and Frankfurt in the first disjunction of hash map 104A) has changed relative to memory 110A, because the hash 00154 is less than the hash 00234. Once the entries or data values are ordered by hash value 108, HMS 101 may generate or assign an index value 112 for each data value 106 or entry corresponding to the order. In the example illustrated, Berlin has been assigned the index value of 0. Also, as illustrated, Frankfurt may include a different index value 112 across different hash maps 104A, 104B. For example, under memory 110B, Frankfurt has index value 1 in hash map 104A, and index value 0 in the same disjunction 102 of hash map 104B.

As illustrated, once the index value 112 has been assigned to each data value 106, the data values 106 may be moved to a disk location 114 arranged by disjunction 102 and by index value 112. For example, the first two values on disk 114 may correspond to the data values 106 from disjunction 102A of hash map 104A (Berlin, Frankfurt), the following data values 106 may be from disjunction 102A of hash map 104B (Frankfurt, Hamburg), the subsequent data values 106 may correspond to the value of disjunction 102B of hash map 104A (Cologne, Mainz), and so on. As illustrated, the values from the various disjunctions are indicated by the brackets 00 (102A), 01 (102B), 10 (102C), and 11 (102D).

In other embodiments, different ordering may be used on the disk 114. For example, the data values across all the disjunctions 102A-D from hash map 104A may be loaded to disk 114 prior to the data values of hash map 104B. In some embodiments, HMS 101 may track which values were moved into which locations on disk 114 from which disjunctions 102 and hash maps 104. In some embodiments, the hash values 108 may be stored as metadata 404 or in another column and may be queried by HMS 101 to identify which data values 106 correspond to which disjunction 102A-D (e.g., the system may query for the hash values for disjunction 102A which may include any hash values beginning with 00).

As illustrated in the example embodiments of FIGS. 1 and 2, two local hash maps were depicted at the same time. The overall number of required local hash maps may be dependent on or correspond to the number of input values. In some embodiments, the size of each local hash maps may be configurable. In some embodiments, HMS 101 may process data with just one local hash map at a time and immediate flush the data out to disk, before the next local hash map is built, to meet minimum main memory requirements.

Figure 3A:
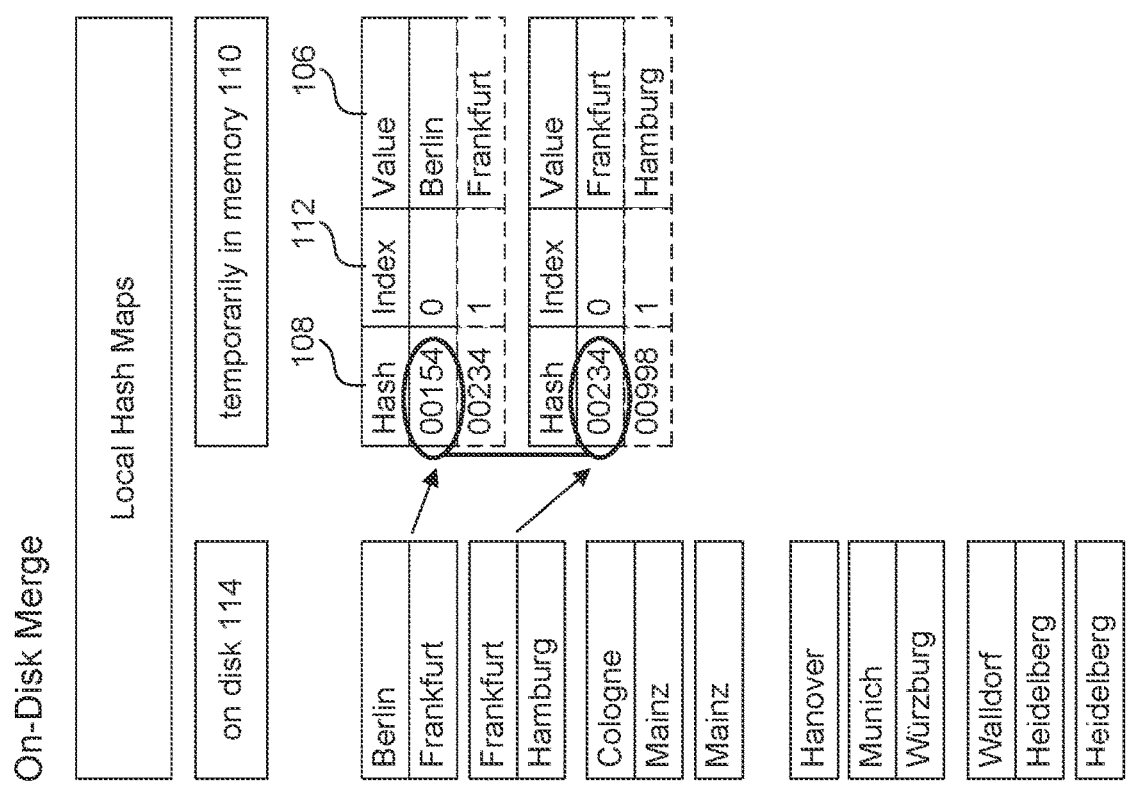
FIGS. 3A-3C illustrate example operations of a hash map merging system (HMS) for performing a disk-based merge with hash maps, according to some embodiments.
Figure 3B:
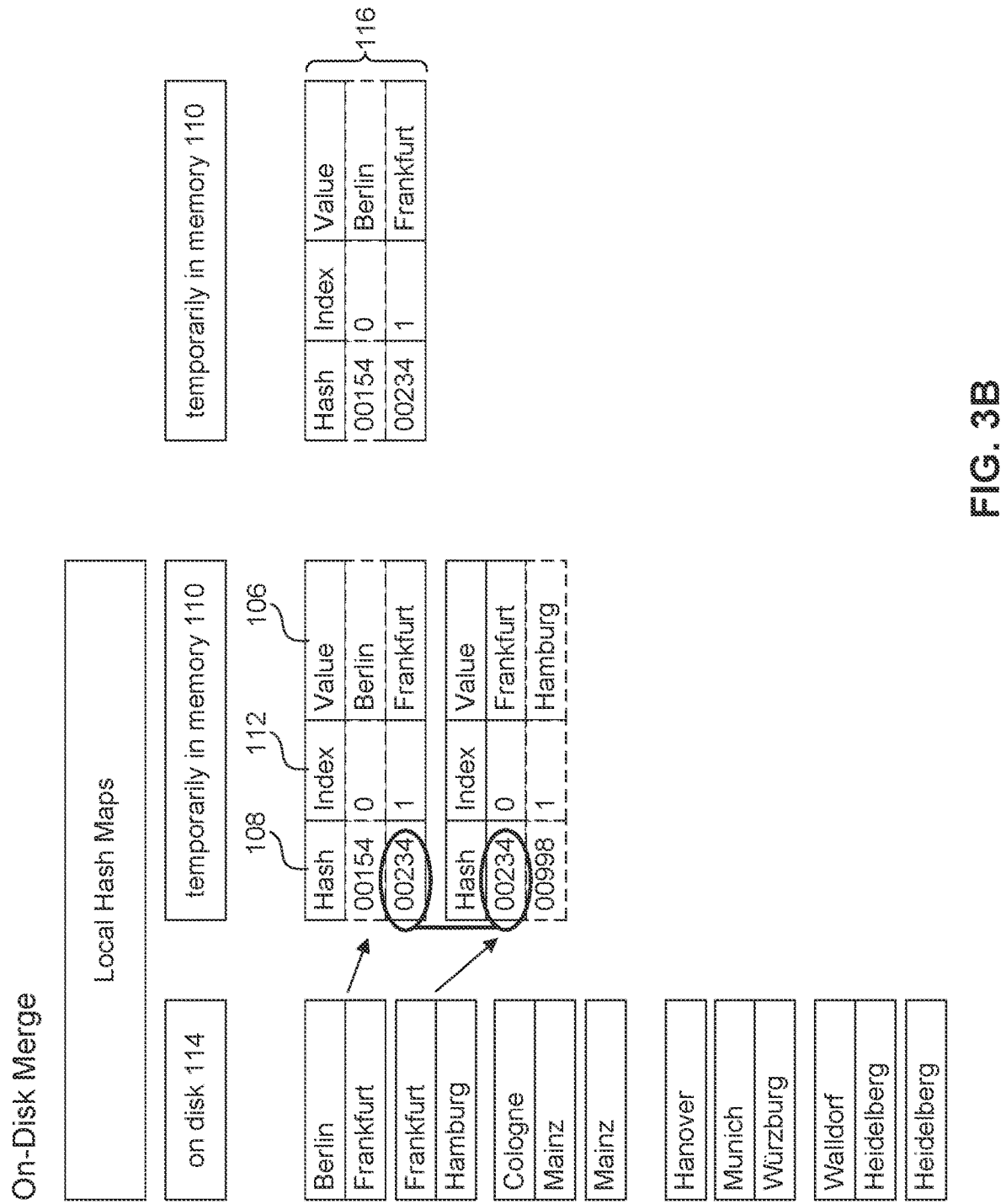
Figure 3C:
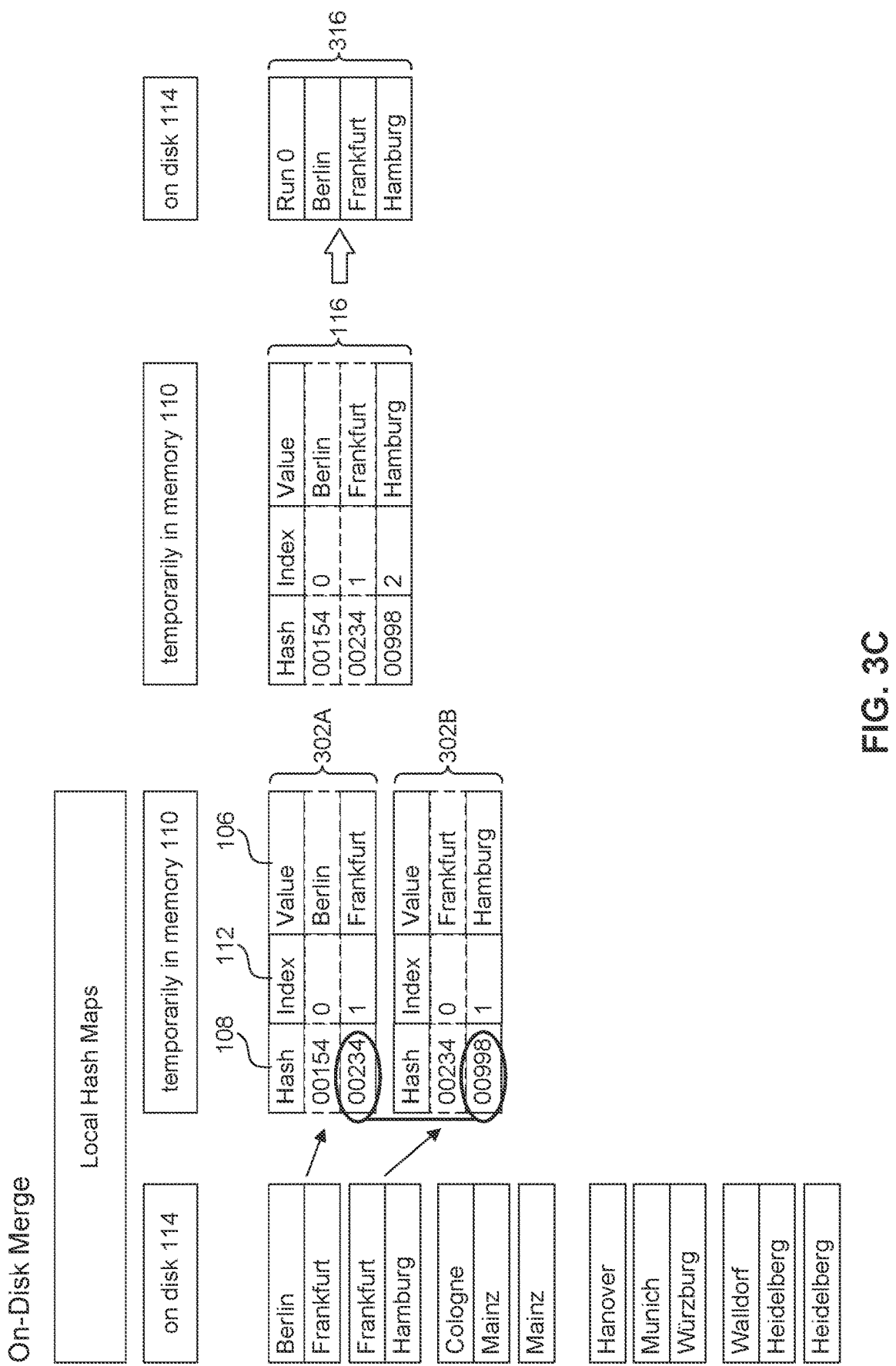

FIGS. 3A-3C illustrate example operations of a hash map merging system (HMS) 101 for performing a disk-based merge with local hash maps, according to some embodiments. In FIG. 3A, the data values from the various local hash maps 104A, 104B may have been stored on disk 114 and ordered or arranged based on their corresponding local hash map 104, disjunction 102, and/or index value (as described above with respect to FIG. 2). FIGS. 3A-3C illustrate example operations related to generating a merged hash map 116, from the original local hash maps 104A, 104B after the values have been arranged and stored on disk 114. In some embodiments, as described herein, disk 114 may refer to non-volatile storage, while memory 110 refers to volatile storage.

In some embodiments, HMS 101 may select a first entry of "Berlin" corresponding to the lowest index value of the first disjunction 102A of the first local hash map 104A, and a first entry of "Frankfurt" with a lowest index value in the first disjunction 102A of the second local hash map 104B.

HMS 101 may move the selected entries corresponding to "Berlin" and "Frankfurt" (with the lowest index values) from disk 114 to memory 110, with their corresponding hash value and index value (e.g., which may have been stored on disk 114, or in metadata 405). In some embodiments, a hash value may be re-calculated on the fly and the index value may be implicitly determined based on the entry's location on disk.

In some embodiments, HMS 101 may compare the hash values 108 of the entries (with the lowest index values) that have been moved to memory 110. The lowest hash value amongst the compared entries may then be identified based on the comparison, selected, and moved to a merged hash map 116. In this example, Berlin has a lower hash value (00154) than Frankfurt (00234), and may be moved into merged hash map 116. Since Berlin is the first entry in the merged hash map 116, Berlin may be assigned a new index value or merged index value of 0.

For simplicity, the illustrated example shows two local hash maps 104A, 104B being merged. However, in other embodiments, more than two hash maps 104 may be merged, in which case the entry with the lowest index value from the first disjunction (102A) across other local hash maps 104 may also be selected and moved into memory 110 and be compared to determine the first entry in merged hash map 116.

In FIG. 3A, the second entries for Frankfurt and Hamburg may not be loaded into memory 110 (as denoted by the dashed line boxes) at the same time as the values of Berlin and Frankfurt (as displayed in the solid line boxes), since Frankfurt and Hamburg are not part of the first comparison (e.g., they do not have the lowest index values). In some embodiments, HMS 101 may minimize how much data is loaded into memory 110 at once may make efficient use of memory 110 and free up memory 110 for other applications thus improving overall system efficiency, functionality, and throughput. However, in other embodiments, is there is a surplus of memory 110 available (e.g., beyond a threshold), then multiple values from the disjunction 102A may be moved into memory 110, which may minimize the number of reads from disk 114, which may also improve processing speeds by utilizing available memory space 110. For example, HMS 101 may load all four illustrated entries (from the first disjunction 102 of the hash maps 104) into memory 110.

In FIG. 3B, the next entry from the disjunction 102A and hash map 104A corresponding with the next lowest index value ("Frankfurt") may be moved from disk 114 onto memory 110 (if not already loaded), and the Berlin entry (as denoted by the dotted line boxes) may have been moved from memory 110 to a version of the merged hash map 116 stored on disk 114 (this version is not separately illustrated in the FIG. 3B, but is denoted by the dashed line boxes in merged hash map 116). The HMS 101 may now compare the hash values of Frankfurt and Frankfurt as illustrated. In this case, there is a hash value match, and as such, the entry "Frankfurt" may be moved into and added to the merged hash map 116, as illustrated. Frankfurt may then be assigned the next lowest available, unassigned, index value of 1. In some embodiments, the hash value collisions may be accounted for or resolved in a deterministic fashion.

As noted above, and as illustrated by the dashed line box, in some embodiments, the first merged hash map entry of Berlin may be moved from memory 110 to disk 114 since it is no longer needed in memory 110. Moving the Berlin entry to disk 114 prior to or after Frankfurt is written to the merged hash map 116 in memory 110 may help free up memory 110 for other applications.

In some embodiments, HMS 101 may maintain both a disk version of merged hash map 116, and an in-memory version of merged hash map 116 while merged hash map 116 is being generated. In some embodiments, the movement of values of merged hash map 116 from memory 110 to disk 114 may occur after a threshold number of values (e.g. 100 values) have been stored on merged hash map 116 in memory 110.

In FIG. 3C, Frankfurt from the in memory hash map 302B may be removed from the memory 110, to free up memory space, and the next entry or entries with the next lowest remaining index value "Hamburg" may be loaded from disk 114 into memory 110, as illustrated.

As described above with respect to FIG. 3B, both in-memory hash maps 302A and 302B had identical hash values for Frankfurt. As such, the value Frankfurt may also be removed from in memory hash map 302A, and the next value in the disjunction 102A for that hash map 302A could be loaded into memory 110. However, in the example illustrated, there are no remaining values for the disjunction 102A for the in-memory hash map 302A (corresponding to the hash map 104A). In some embodiments, Frankfurt from in-memory hash map 302A may still be removed from memory 110 to free up additional memory space. Because Hamburg is the only remaining entry for disjunction 102A (across the hash maps 302A, 302B), this entry can be added to merged hash map 116. Once the disjunction 102A has been completed, HMS 101 may repeat this process for the entries of the next disjunction 102B of the remaining disjunctions 102B-D. HMS 101 may then continue this process until all the entries of all the disjunctions 102A-D of all the hash maps 104 have been processed, compared, and accounted for in merged hash map 116.

One of the advantages of this merging process is that the HMS 101 does not require an entire hash map 104A, 104B to be loaded into memory to build or generate the merged hash map 116. Instead, the HMS 101 utilizes memory 110 very efficiently, by pre-ordering the values and storing those entries on disk, as described above. The HMS 101 may then efficiently only load a relevant subset of the pre-ordered values from the disk 114 onto memory 110 for comparison, and generating the merged hash map 116. However, if there is excess memory space available, HMS 101 can load more values at once into memory, which may minimize the reads from disk 114, which may help further increase processing speeds, the speed of generating the merged hash map 116, and overall system throughput.

As described above, HMS 101 may periodically move one or more entries from the merged hash map 116 from memory 110 to disk 114, to further free up memory space and allocations. As illustrated in FIG. 3C, when doing the comparison for Hamburg, there may be a version of the merged hash map 116 stored on disk with the entries of Berlin and Frankfurt. Then, when Hamburg is identified as the next entry, the Hamburg entry may be appended to the merged hash map 116 as stored on disk 114, which may further help increase and improve memory utilization and reduce the memory footprint that may be required in generating or building a merged hash map 116. In some embodiments, the merged hash map 116 may be built entirely on disk 114, one entry at a time.

As illustrated by on-disk merged hash map 316, the merged hash map 116 may be further streamlined by removing the index value, since the position of each data value in the merged hash map 116 is indicative of its position. On-disk merged hash map 316 may represent a streamlined version of the original merged hash map 116, without the index value. In some embodiments, the hash value for each data value may be stored as metadata 405 associated with the on-disk merged hash map 316. Removing this extra information may allow disk merged hash map 316 to consume less disk space, and less memory space when on-disk merged hash map 316 is loaded into memory 110 for use (e.g., in processing queries).

In some embodiments, the streamlined or disk merged hash map 316 may also include a title or label "Run 0" indicative an order or time when the merged hash map was created or generated as provided by HMS 101. "Run 0" is an example label, however any label or title from which an order may be implied between different hash maps may be used. For example, the title may be "A" or may be a date/time stamp, etc. This title or label of the merged hash map 316 may be used when the values of hash maps are updated and new merged hash maps 316 are generated or created, as is described in greater detail below. The title and ordering indicated by the title may also be used when combining streamlined or disk merged hash maps 316, as also described in greater detail below.

FIG. 4 is a block diagram 400 illustrating a hash map merging system (HMS) 101, according to some example embodiments. As described above with reference to FIGS. 1-3C, HMS 101 may perform a merging between different hash maps 104A and 104B and generate or build a merged hash map 316. The merged hash map 416 may be used for lookups and enable HMS 101 or another computing system utilizing the merged hash map 316 to perform faster query processing, thus increasing system throughput. Additionally, as described herein, HMS 101 generates merged hash map 316 while making efficient use of memory 110.

In some embodiments, an ordering engine 402 includes one or more computing processors that are configured to perform comparison and ordering operations on the data values 106, hash values 108, and index values 112 used throughout the merging operations as described herein. For example, ordering engine 402 may order the various entries (e.g., data value 106, index value 112, hash value 108) or data values 106 in a particular disjunction 102, by the hash value 108.

In some embodiments, an indexing engine 404 includes one or more computing processors that are configured to assign, add, remove, or store (e.g., in metadata 405) index values 112 for the various entries of hash values 108 and/or data values 106 during the merging operations described herein.

Metadata 405 may include information about the various entries (e.g., data values 106, hash values 108, and/or index values 112) that is maintained by HMS 101, and which may be used in the merging operations described herein.

Hash function 420 may include a hashing algorithm that is used to generate the hash values 108 form the data values 106, as described herein.

In some embodiments, HMS 101 may receive a command or query 406 for a particular value (e.g., index value 112 or data value 106), and using the merged hash map 316, HMS 101 may process the query 406 and return a result 408. The computing operations in using the merged hash map 316 to respond to query 1406 may be faster than query operations using multiple different local hash maps 104A, 104B with overlapping values, as described above, and as may have been present prior to ordering, merging, or combining as described herein.

Figure 5:
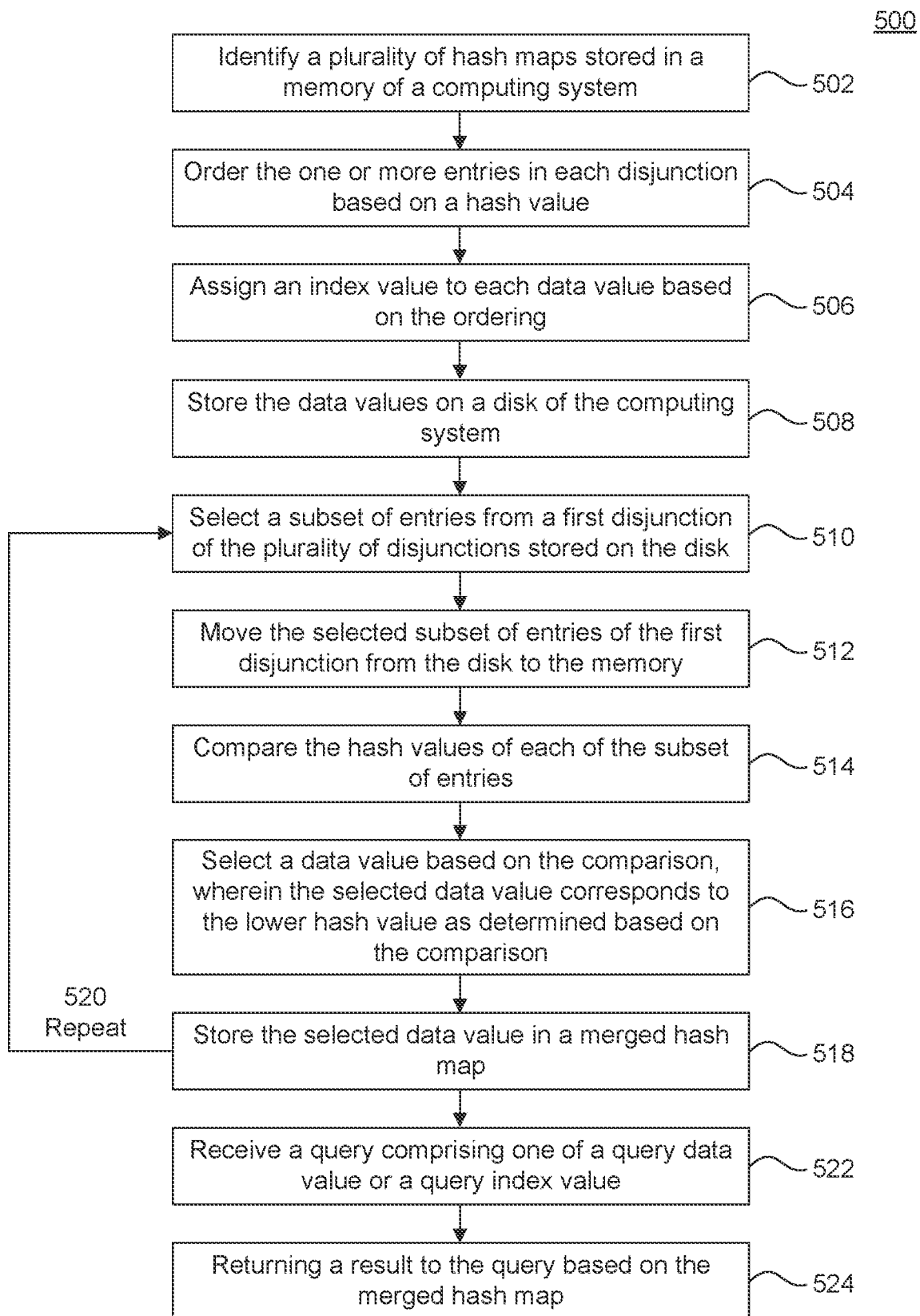
FIG. 5 is a flowchart illustrating a process for a hash map merging system (HMS), according to some embodiments.

FIG. 5 is a flowchart illustrating a process 500 for a hash map merging system (HMS) 101, according to some embodiments. Method 500 can be performed by processing logic that can comprise hardware (e.g., circuitry, dedicated logic, programmable logic, microcode, etc.), software (e.g., instructions executing on a processing device), or a combination thereof. It is to be appreciated that not all steps may be needed to perform the disclosure provided herein. Further, some of the steps may be performed simultaneously, or in a different order than shown in FIG. 5, as will be understood by a person of ordinary skill in the art. Method 500 shall be described with reference to the figures.

In 502, a plurality of hash maps stored in a memory of a computing system are identified. For example, in FIG. 1 memory 110 includes hash maps 104A and 104B. Each hash map 104 includes disjunctions 102A-D. And within each disjunction 102 includes one or more entries including a data value 106 and a corresponding hash value 108.

In 504, the one or more entries in each disjunction is ordered based on the hash value. For example, in FIG. 2, Berlin and Frankfurt in hash map 104A are sorted, ordered, arranged, or reordered by an ordering engine 402 (of FIG. 4) based on hash value 108.

In 506, an index value is assigned to each data value based on the ordering. For example, in FIG. 2, the hash values 108 may be moved into metadata 405 (of FIG. 4), and indexing engine 404 may assign index values 112 to each entry in the ordered hash tables 104A, 104B illustrated in memory 110B.

In 508, the data values are stored on a disk of the computing system. For example, in FIG. 2, the data values are moved from the memory 110B and stored on disk 114, as illustrated on the right-hand side of the image. The data values may be grouped by disjunction 102 and ordered based on their assigned index value 112. For example, the first two data values (Berlin, Frankfurt) may be from disjunction 102A of hash map 104A, the next two data values (Frankfurt, Hamburg) may be from disjunction 102A of hash map 104B, etc. In some embodiments, HMS 101 may maintain a mapping of which values from which disjunction 102 are stored in which disk locations.

In 510, a subset of entries are selected from a first disjunction of the plurality of disjunctions stored on the disk. For example, as illustrated in FIG. 3A, the entry for Berlin is selected from disjunction 102A of hash map 104A, and the entry for Frankfurt is selected from disjunction 102A of hash map 104B. These entries may be those entries from each disjunction 102 with the smallest index value.

In 512, the selected subset of entries of the first disjunction are moved from the disk to the memory. For example, as illustrated by the solid line boxes, the entries for Berlin and Frankfurt may be moved to memory 110.

In 514, the hash values of each of the subset of entries are compared. For example, in FIG. 3A, the ordering engine 402 (from FIG. 4) may compare the hash values 108 and identify the lowest hash value (of the compared values) as corresponding to the Berlin entry.

In 516, a data value is selected based on the comparison, wherein the selected data value corresponds to the lower hash value as determined based on the comparison. For example, comparison engine 402 may, in FIG. 3A, select the Berlin entry with the lowest hash value 108 between the compared hash values. In other embodiments, more than two hash values may be compared if there were more than two hash maps.

In 518, the selected data value is stored in a merged hash map. For example, HMS 101 may store the entry for Berlin in the merged hash map 116, as illustrated in FIG. 3A.

In 520, the process from 510-518 is repeated until all the data values have been compared. For example, as illustrated in FIGS. 3B and 3C, the process is repeated for a subset of the values, however it is understood the same process may be repeated until all of the values across the hash maps 104 have been accounted for and stored in the merged hash map 116. As described above, and as illustrated by FIGS. 3A-3C, different values and entries may be moved into and out of memory 110 and onto and from disk 114 to minimize the amount of memory 110 being used during the merging process.

In 522, a query comprising one of a query data value or a query index value is received. For example, as illustrated in FIG. 4, HMS 101 may receive a query 406 which may include one or more index values or data values. In some embodiments, the query 406 may include a read, edit, or write command.

In 524, a result to the query is returned based on the merged hash map. For example, HMS 101 or another computing system may access or move merged hash map 316, which may have been moved into memory 110, to process the query 406, and return a result 408 including the requested value(s).

FIGS. 6A-6D illustrate example operations related to creating a new merged hash map, according to some example embodiments. While HMS 101 is generating merged hash map 316 and/or after HMS 101 has generated merged hash map 316, a computing system (which may or may not be HMS 101) may have continued operations with regards to adding and removing values from a database or data storage system, and these new data values may be stored in corresponding new hash maps 604A-B may have been added to the system to which HMS 101 has access.

Figure 6A:
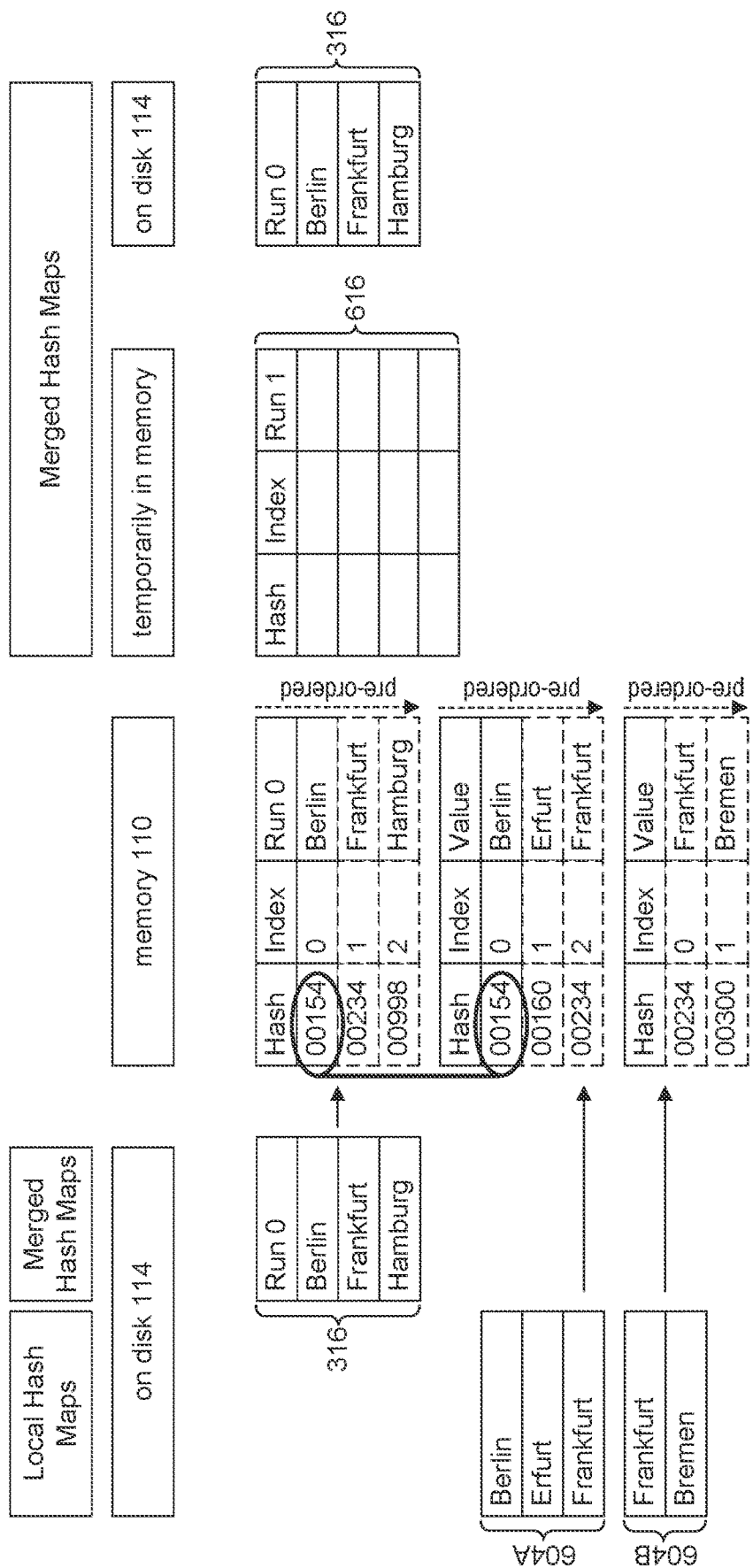
FIGS. 6A-6D illustrate example operations related to creating a new merged hash map, according to some example embodiments.

HMS 101 may periodically execute when new data is ingested into the system. An initial merged hash map ("Run 0") may be created, on a first execution. Over time, perhaps once per day, new data may be ingested. Then, HMS 101 may execute again to incorporate the new data with subsequent runs. In FIG. 6A, on the left side, the initial state of a computing system is illustrated under disk 114. As illustrated, HMS 101 may include or have access to a previously generated merged hash map 316 (with label "Run 0"), and multiple new local hash maps 604A, 604B which may have been created in parallel with or after merged hash map 316 was generated. The operations described with respect to FIGS. 6A-6D illustrate example operations for creating a second merged hash map (e.g., after one or more merged hash maps 316 already exist or have been previously generated).

As illustrated, the operations may begin with merged hash map 316 and new local hash maps 604A, B initially being stored on disk 114. As described above, ordering engine 402 may sort, order, or rearrange the entries of the new local hash maps 604A-B based on their hash values. In some embodiments, indexing engine 404 may assign index values to the ordered entries of 604A, 604B.

When including new local hash maps to the merged hash map, previous values keep their previous index values and new values may be assigned new index values. This may achieved by HMS 101 using the existing merged hash maps as the first or leading hash map in the comparisons that are conducted in the following steps. HMS 101 may select the first entry with the lowest index value (0) from the merged hash map 316 and a first entry with the lowest index value (0) from local hash map 604A, and move the selected entries (Berlin and Berlin) from disk 114 to memory 110 (as illustrated by the solid lines). HMS 101 may then compare the hash values (00154, 00154) from the selected entries. The dashed lines indicate values from disk 114 that may optionally be moved into memory 110, depending on available memory 110 capacity, or may remain on disk 114 during the comparison as described below.

Based on the comparison, HMS 101 may identify that the hash value (00154) from the new local hash map 604A matches the hash value from the merged hash map 316. From this matching of the hash values, HMS 101 may determine that the data value (Berlin) is already accounted for in the merged hash map 316, and that the value from the local hash map 604A does not need to be added to the new secondary merged hash map 616. In some embodiments, Berlin from local hash map 604A may be evicted from memory 110 at this time, or at a later time without adding a new entry to secondary merged hash map 616.

Figure 6B:
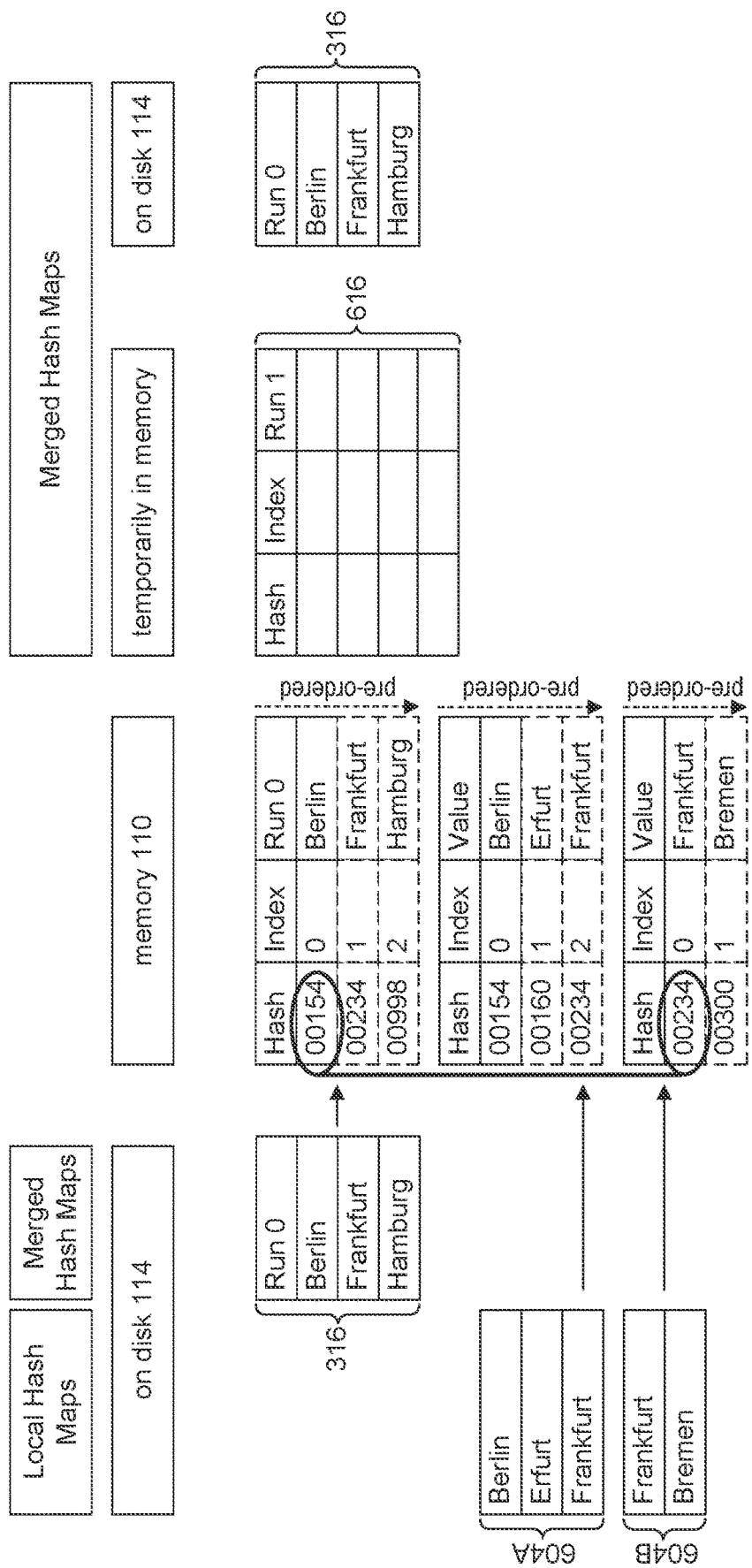

As illustrated in FIG. 6B, the first entry with the lowest index value (0) from the local hash map 604B is loaded into memory 110, and its hash value is compared to the hash value of Berlin from the merged hash map 316, which had the lowest index value. HMS 101 may determine that the hash value of Berlin (00154) is less than the hash value of Frankfurt (00234). Based on this determination, HMS 101 may load the next entry (with the next lowest index value—1) from the merged hash map 316 on disk 114 into memory 110, as illustrated in FIG. 6C.

HMS 101 may then compare the hash value (00234) of the next entry (Frankfurt) from merged hash map 316 to the hash value (00234) for Frankfurt from local hash map 604B. HMS 101 may determine that the hash values match or are identical. Based on this determination, HMS 101 may determine that the data value (Frankfurt) corresponding to the hash value 00234 is already stored in merged hash map 316, and does not need to be included in the new merged hash map 616. In this way, HMS 101 is able to avoid storing the same entry or data value across multiple merged hash maps (616, 316).

Figure 6C:
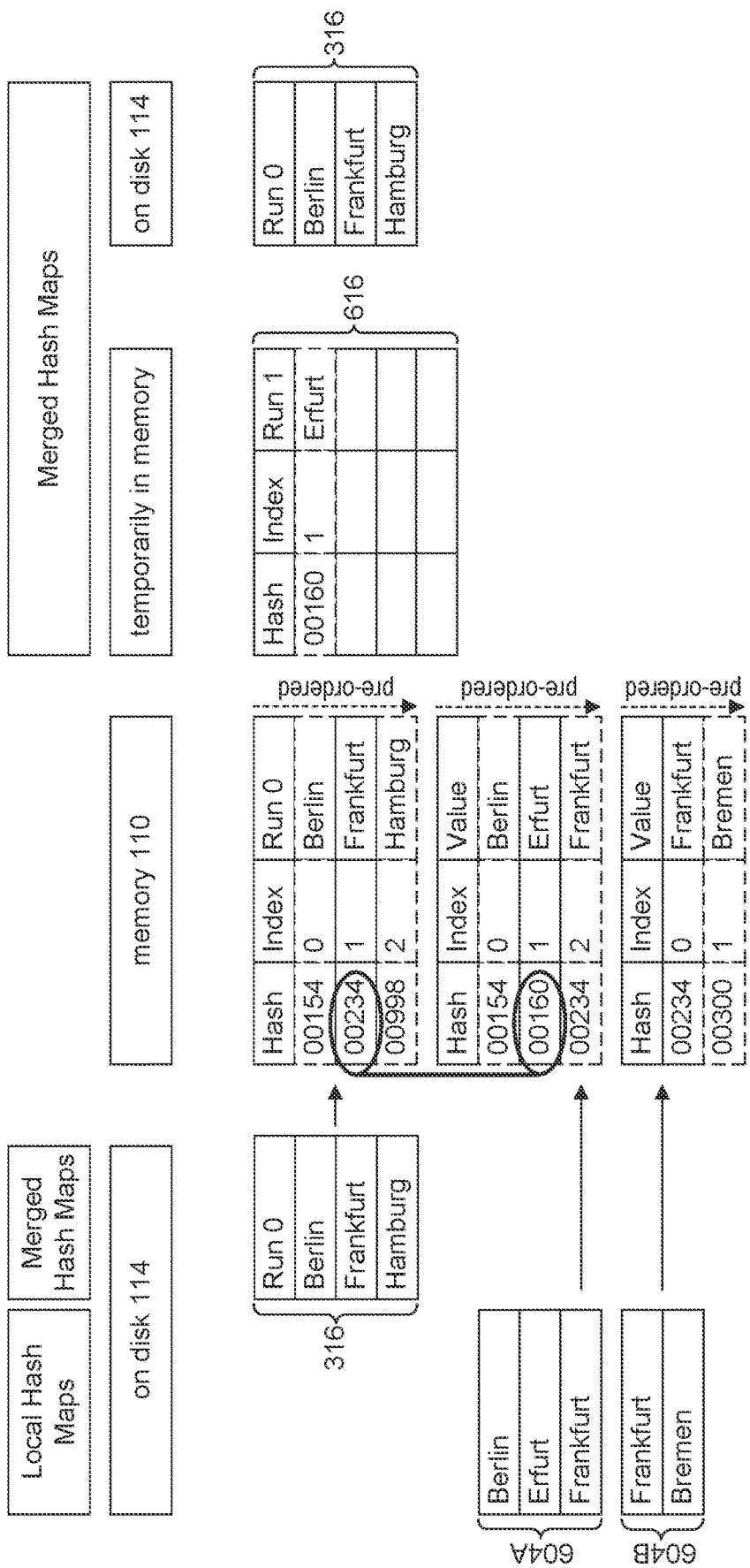

As illustrated In FIG. 6C, the hash value (00234) of merged hash map 316 may then be compared to the hash value (00160) of the next smallest index value (1) from local hash map 604A. HMS 101 may identify a mismatch between the hash values, and determine that the hash value 00160 is less than the hash value 00234 of merged hash map 316. Based on this determination that the hash value of new local hash map 104 is less than the present hash value from the merged hash map 316, HMS 101 determine that the entry corresponding to the low hash value from local hash map 106 needs to be added to the new or secondary merged hash map 616. HMS 101 may then store the entry from the local hash map 604A for Erfurt in the new or secondary merged hash map 616 (as illustrated in the dashed line box of 616).

The process described above, with respect to loading new entries from disk 114 to memory 110, for each of the entries from both merged hash map 316 and the local hash maps 604A-B may be repeated until all the values of the local hash maps 604A-B have been accounted for and stored in either merged hash map 316, or secondary merged hash map 616. In some embodiment, entries added to 616 may immediately be flushed to disk and the memory freed to preserve a small memory footprint.

Figure 6D:
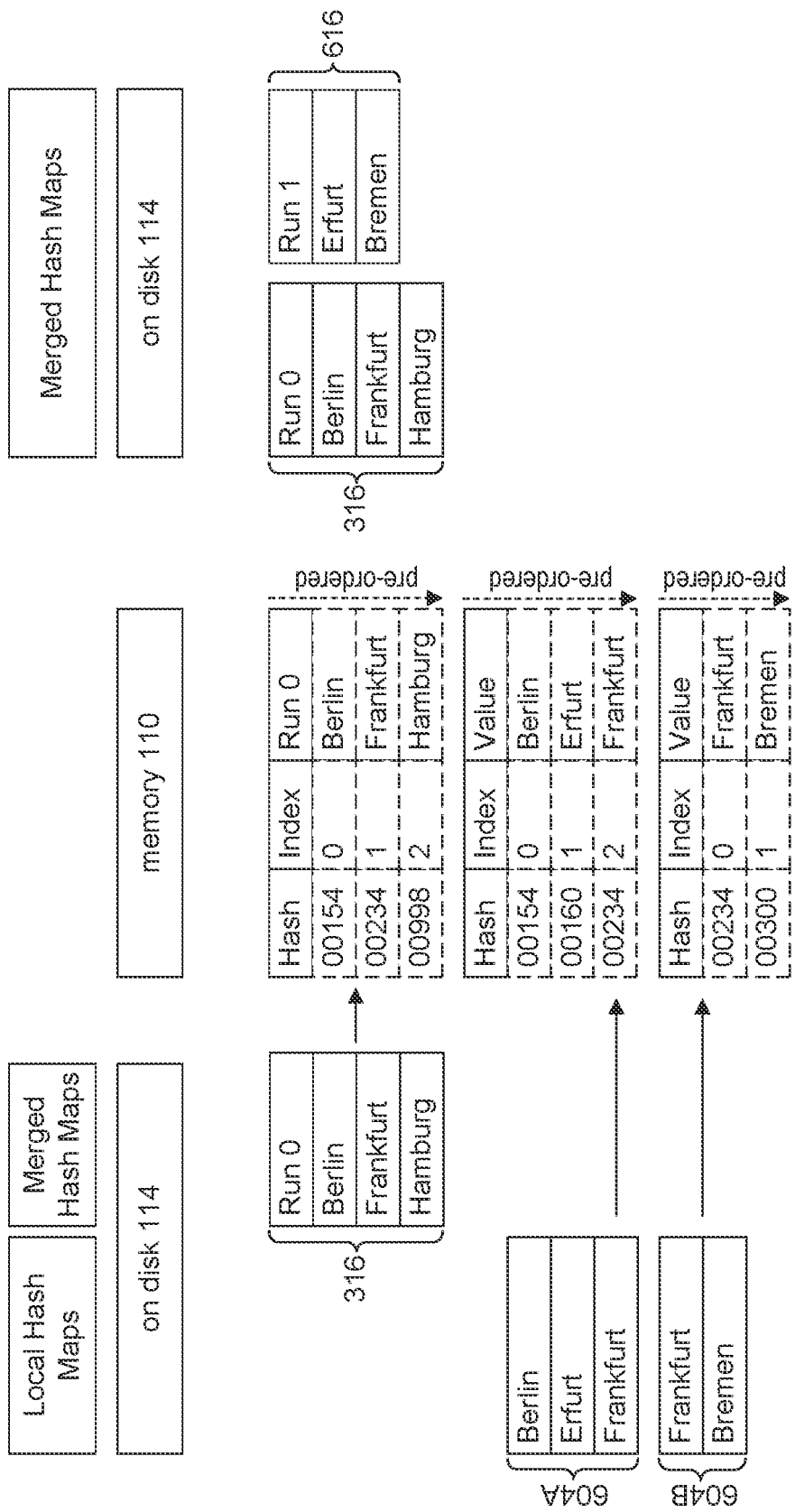

As illustrated in FIG. 6D, the result of the above-described processing of FIGS. 6A-C may be two resultant merged hash maps 316 and 616. As illustrated, secondary merged hash map 616 may be labeled Run 1, while the first, original, or previous merged hash map 316 may be labeled Run 0. These labels or metadata 405 about each merged hash map 316, 616 may enable HMS 101 track the order in which the merged hash maps 316, 616 were created which may be relevant for indexing (as described in further detail below), and may provide other utility as well. For example, while the indexes for the values in the first merged hash map 316 ("Run 0") may be 0-2, HMS 101 may assign indexes 3 and 4 for the values in the secondary hash map 616 ("Run 1") may be 3 and 4, respectively. In some embodiments, HMS 101 may also maintain a count of how many entries are in each merged hash map 316, 616. The counts would respectively be 3 and 2.

In some embodiments, HMS 101 may receive a new set of local hash maps generated after secondary merged hash map 616. During this processing, HMS 101 may compare the values of both merged hash maps 316, 616 to each of the values of the new local hash maps (not illustrated) until all the new values have been matched to a preexisting value in merged hash map 316, second merged hash map 616, or a new merged hash map which may be labeled Run 2.

In some embodiments, HMS 101 may receive a query 406 (as illustrated in FIG. 4) while the multiple merged hash maps 316 and 616 are maintained on disk 114. As an example, the query 406 may include the data value "Hamburg" and may request the corresponding index value. HMS 101 may first hash the data value ("Hamburg") of query 406 to produce the corresponding hash value (00998) for Hamburg.

Then, for example, HMS 101 may perform a binary search on the Run 0 (first merged hash map 316). The result of the binary search may be to identify Hamburg in position 3, based on the hash value. HMS 101 may then return the corresponding index value of 2.

Or, for example, query 406 (or a different query 406) may request the index value for "Bremen". HMS 101 may generate the hash value for Bremen (00300), and apply binary search to Run 0. The result of the binary search may be a null set, or other indication that the hash value 00300 was not found in the merged hash map 316.

HMS 101 may then apply the binary search for 00300 to Run 1 (secondary merged hash map 616—which may be loaded into memory 110 after Run 0 is evicted from memory 110, in order to conserve memory space), and may identify Bremen in position 2. Because the index values in Run 1 are a contiguous set or a continuation of the index values from Run 0 (thus highlighting the value of the labels indicating an order between the hash maps), the index value for Bremen in position 2, is index value 4 which is returned as the result 408. In some embodiments, HMS 101 may load both merged hash maps 316, 616 into memory 110 and execute binary searches on Run 0 and Run 1 in parallel for a particular hash value—which may consume more memory but increase processing speeds. In some embodiments, HMS 101 may not load any merged hash maps into memory, but instead conduct the binary search by means of on-disk seek operations.

In some embodiments, query 406 may include an index value, such as index value 4. Then, for example, based on the maintained metadata 405 about the merged hash maps 316, 616 indicating their order and count of values, HMS 101 may quickly determine that index value 4 is not in Run 0 (whose first index value is 0 and count is 3), but is in Run 1, in position 2 (whose first index value is 3, and count is 2), and may return the corresponding value "Bremen" as result 408.

Figure 7A:
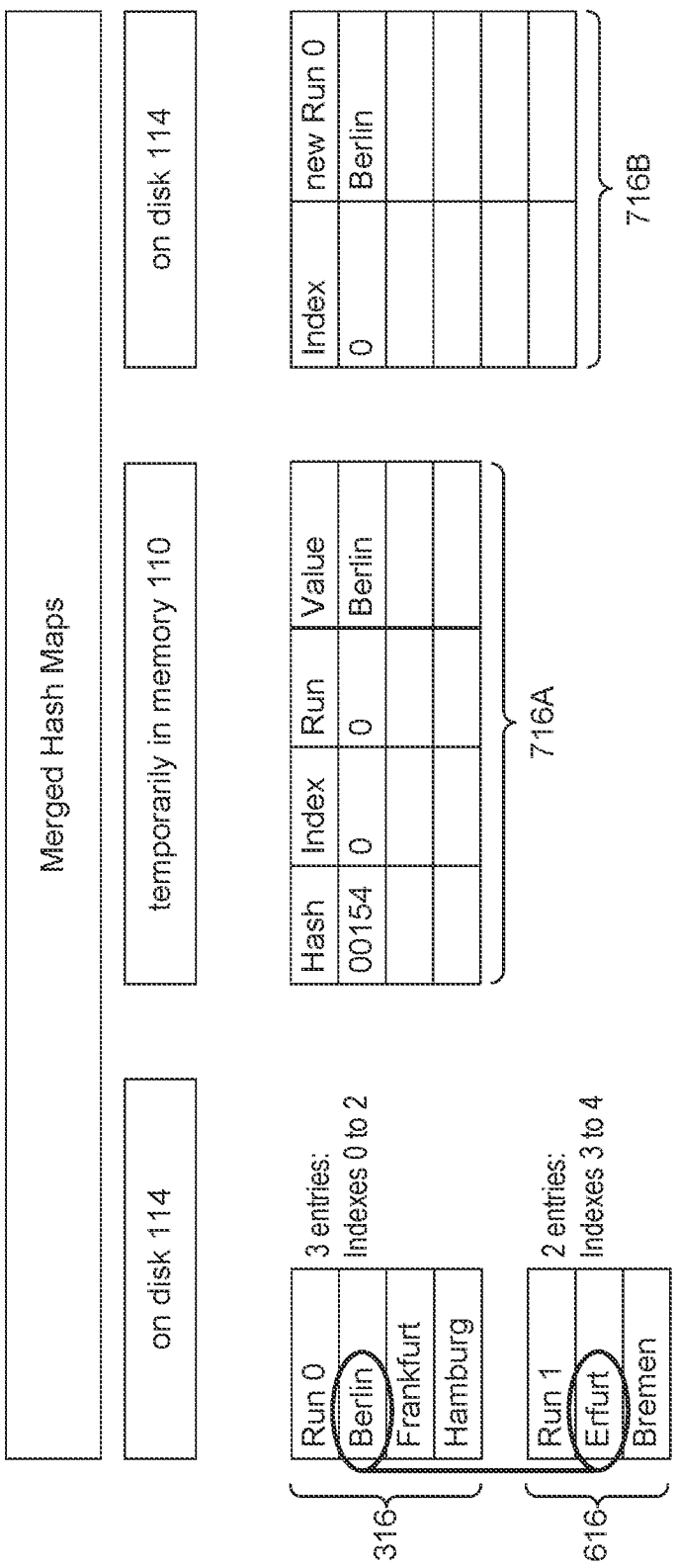
FIGS. 7A-7C illustrate example operations related to creating a combined hash map, according to some example embodiments.
Figure 7B:
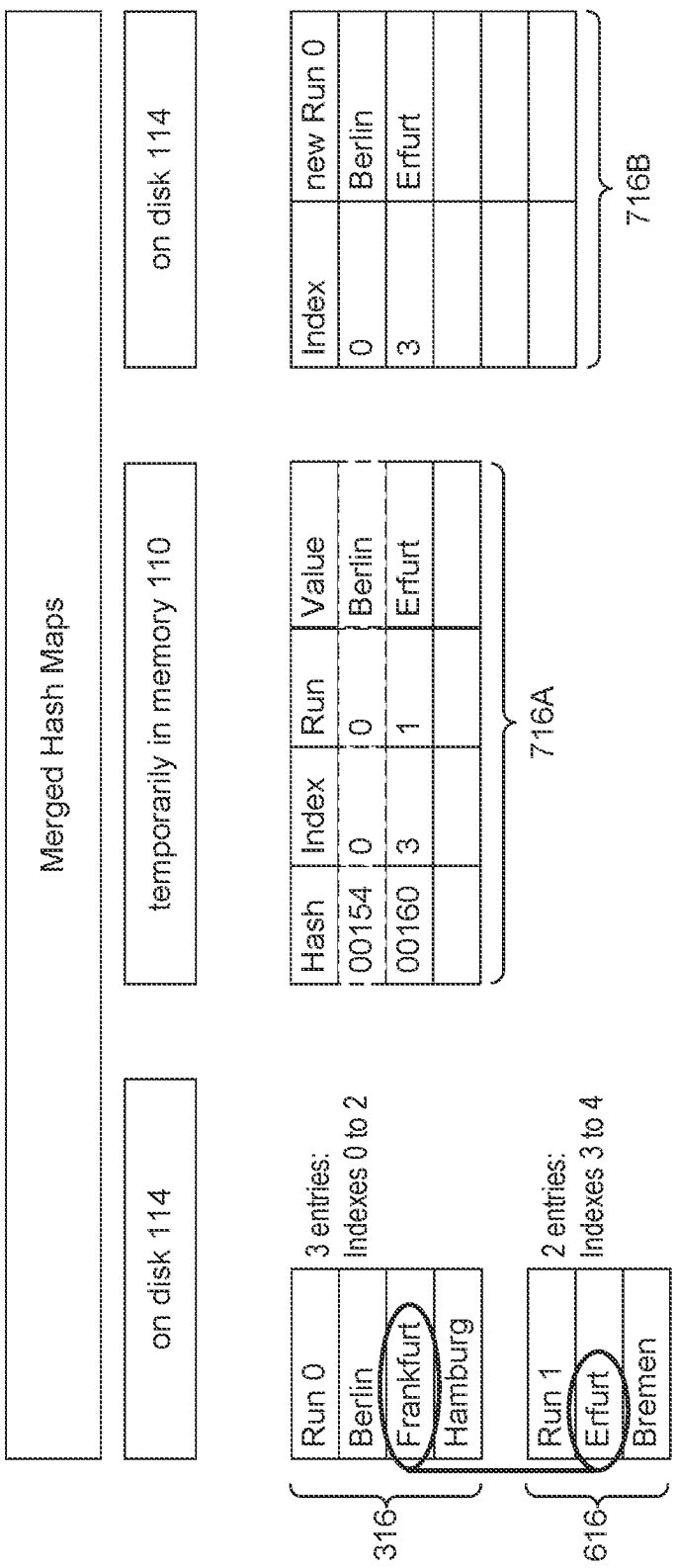
Figure 7C:
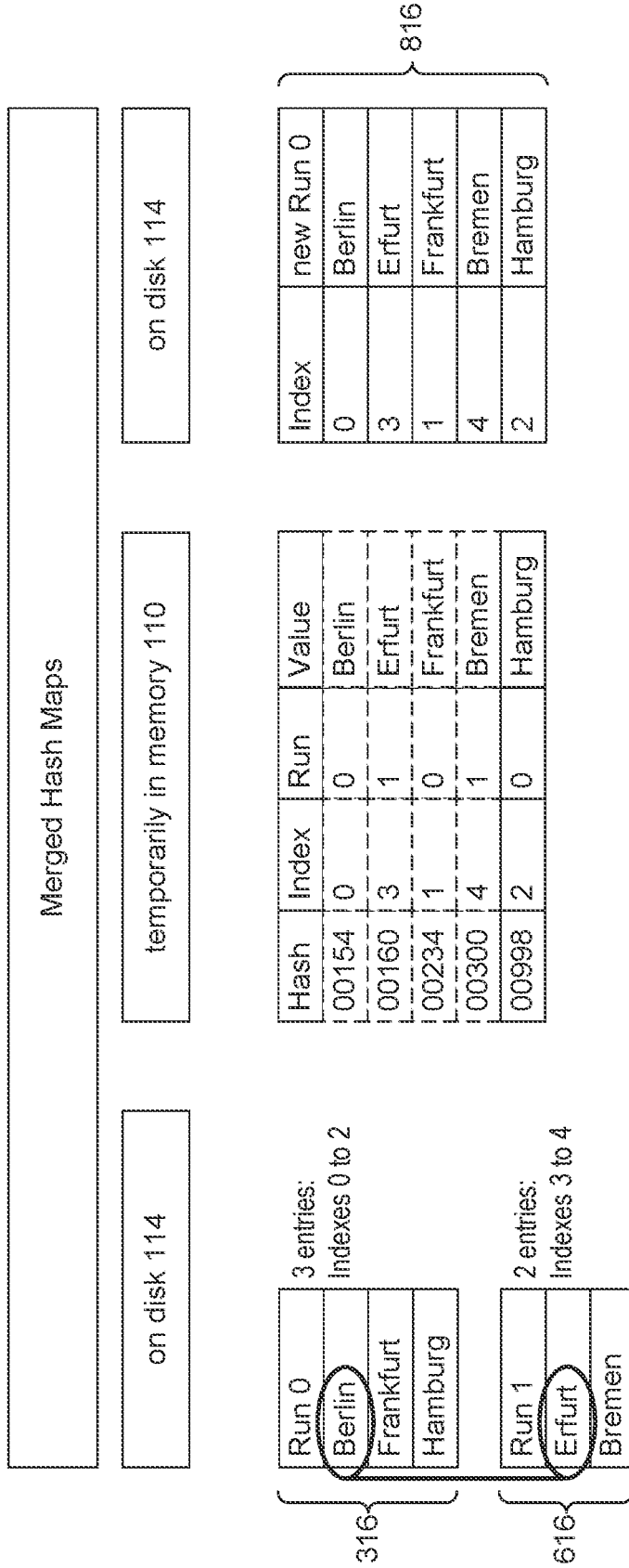

FIGS. 7A-7C illustrate example operations related to creating a combined hash map, according to some example embodiments. As described above, HMS 101 may create or generate multiple merged hash maps 316, 616 (which are illustrated in FIG. 7A, as an initial state, under disk 114). HMS 101 may also process queries 406 using the multiple merged hash maps 316, 616. However, processing a query 406 using multiple hash maps 316, 616 may be less efficient than processing the same query 406 using a single combined hash map 716.

FIG. 7A illustrates combined hash map 716A and combined hash map 716B, which may be referred to together, individually, and/or generally as combined hash map 716. Combined hash map 716A may illustrate a first stage of processing (on memory 110), while combined hash map 716B illustrates a second stage of processing (on disk 114). FIGS. 7A-7C illustrate example processes, as performed by HMS 101, for combining multiple merged hash maps 316, 616 into a single combined hash map 716.

As described above, each merged hash map 316, 616 may be ordered by index value. In some embodiments, as illustrated in FIG. 7A, HMS 101 may select and compare the first hash value (with the lowest index value) from each merged hash map 316, 616, to identify the entry with the lowest hash value. HMS 101 may store the entry with the lowest hash value in combined hash map 716A (which may temporarily be stored in memory 110).

For example, Berlin may have a lower hash value than Erfurt, and may be stored in intermediate combined hash map 716A. In some embodiments, to optimize memory 110 allocations, HMS 101 may then move the entry (Berlin) from combined hash map 716A in memory 110 into combined hash map 716B on disk 114.

As described herein, combined hash map 716A and combined hash map 716B, may represent two different stages of a single combined hash map. In some embodiments, the initial combined hash map 716A as stored in memory 110 may include more information than the resultant combined hash map 716B that is stored on disk 114. For example, the run information (e.g., Run 0 or Run 1) may no longer be relevant for combined hash map 716B, and may not be stored on disk 114. Similarly, because the hash value may be easily attained (e.g., by providing a data value to the hash algorithm or hash function 420 used by HMS 101, to save disk storage space (and memory storage space when combined hash map 716B is moved back into memory for use at a later time), combined hash map 716B may not include the hash value. In some embodiments, HMS 101 may include the hash value with resultant combined hash map 716B.

As illustrated in FIG. 7B, HMS 101 may then compare the next hash value corresponding to the next lowest index for Frankfurt in Run 0 to the hash value for the Erfurt entry in Run 1. Similar to what was described above with respect to FIG. 7A, the entry with the lower hash value may be moved into combined hash map 716A (Erfurt), and to save memory storage space, the previous entry of Berlin may have been evicted from memory 110 (as indicated by the dashed lines). In some embodiments, HMS 101 may also move the Erfurt entry into combined hash map 716B on disk 114.

In some embodiments, HMS 101 may not move every entry into combined hash map 716A directly into combined hash map 716B. In some embodiments, HMS 101 may wait a threshold period of time (e.g., 3 seconds), or until a threshold number of entries (e.g., 100 entries) have been stored in initial combined hash map 716A prior to moving the entries to resultant combined hash map 716B on disk.

FIG. 7C illustrates an example completed combined hash map 816 (which may be the result of processing described above with respect to combined hash map 716B). Completed or final combined hash map 816 may be the final version of the hash maps 716A, 716B, post processing all the entries from merged hash maps 316 and 616. As illustrated, completed combined hash map 816 has maintained the index values from the merged hash maps 316.

Then, for example, when a query 406 is received, HMS 101 or another data storage or data retrieval system may use the combined hash map 816 to perform data look ups as described above, and return a result 408. In some embodiments, the combined hash map 816 may be sorted by hash value, and may be searched using binary search in logarithmic time.

Figure 8:
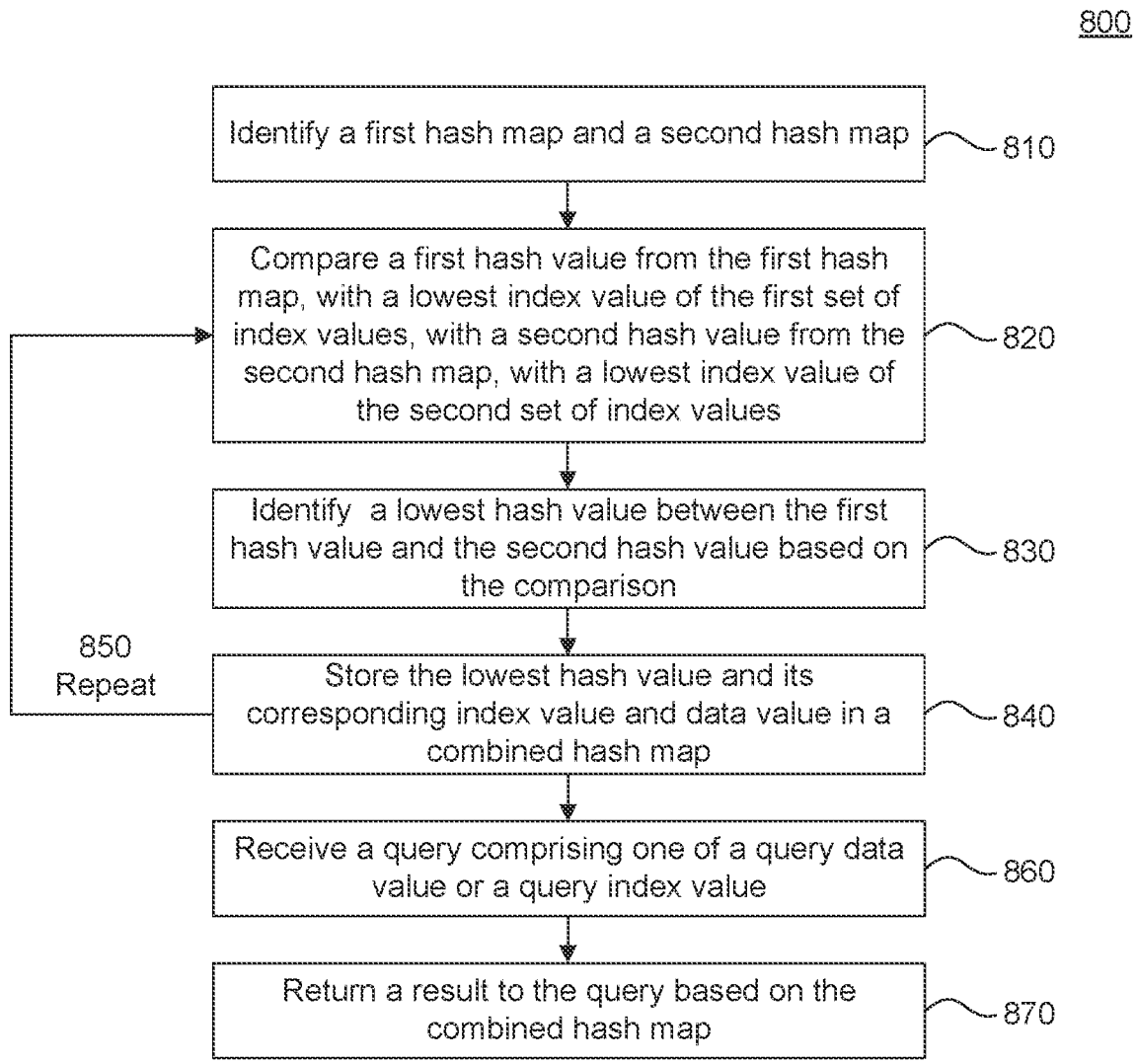
FIG. 8 is a flowchart illustrating a process for combining merged hash maps, according to some embodiments.

FIG. 8 is a flowchart 800 illustrating a process for combining merged hash maps, according to some embodiments. Method 800 can be performed by processing logic that can comprise hardware (e.g., circuitry, dedicated logic, programmable logic, microcode, etc.), software (e.g., instructions executing on a processing device), or a combination thereof. It is to be appreciated that not all steps may be needed to perform the disclosure provided herein. Further, some of the steps may be performed simultaneously, or in a different order than shown in FIG. 8, as will be understood by a person of ordinary skill in the art. Method 800 shall be described with reference to the figures.

In 810, a first hash map and a second hash map are identified. For example, as illustrated in FIG. 7A, HMS 101 may identify merged hash maps 716 and 616 in disk 114. Though not illustrated, HMS 101 may retrieve from metadata 405 the hash values and index values for the data values illustrated under Run 0 and Run 1. In some embodiments, HMS 101 may regenerate the hash values using the hash algorithm 420, if the hash values are not available in metadata 405.

In 820, a first hash value from the first hash map, with a lowest index value of the first set of index values, is compared with a second hash value from the second hash map, with a lowest index value of the second set of index values. For example, as illustrated in FIG. 7A, HMS 101 may compare the hash value of Berlin to the hash value for Erfurt.

In 830, a lowest hash value between the first hash value and the second hash value is identified based on the comparison. For example, based on comparing the hash values of Berlin (00154) and Erfurt (00160), HMS 101 may identify Berlin as having the lower hash value.

In 840, the lowest hash value and its corresponding index value and data value are stored in a combined hash map. For example, HMS 101 may store the entry with the lowest hash value in the combined hash map 716A.

In 850, the comparing, identifying the lowest hash value, and storing for both the first set of hash values and the second set of hash values is repeated until all of the hash values from both the first set of hash values and the second set of hash values are stored in the combined hash map. For example, as illustrated in FIGS. 7B-7C, the hash values for the remaining (unprocessed) data values are compared, and stored in the intermediary combined hash map 716A, and moved into the intermediary combined hash map 716B. Once all the values have been processed, HMS 101 may use combined hash map 816 to perform query processing.

In 860, a query comprising one of a query data value or a query index value is received. For example, HMS 101 may receive a query 406 which may include one or more data values (for which the corresponding index value is sought) and/or one or more index values (for which the corresponding data value is sought).

In 870, a result to the query is returned, wherein the query was processed based on the combined hash map. For example, HMS 101 or another data processing system may process query 406 to generate the result 408 (e.g., the requested data value or index value) using the combined hash map 816.

Figure 9:
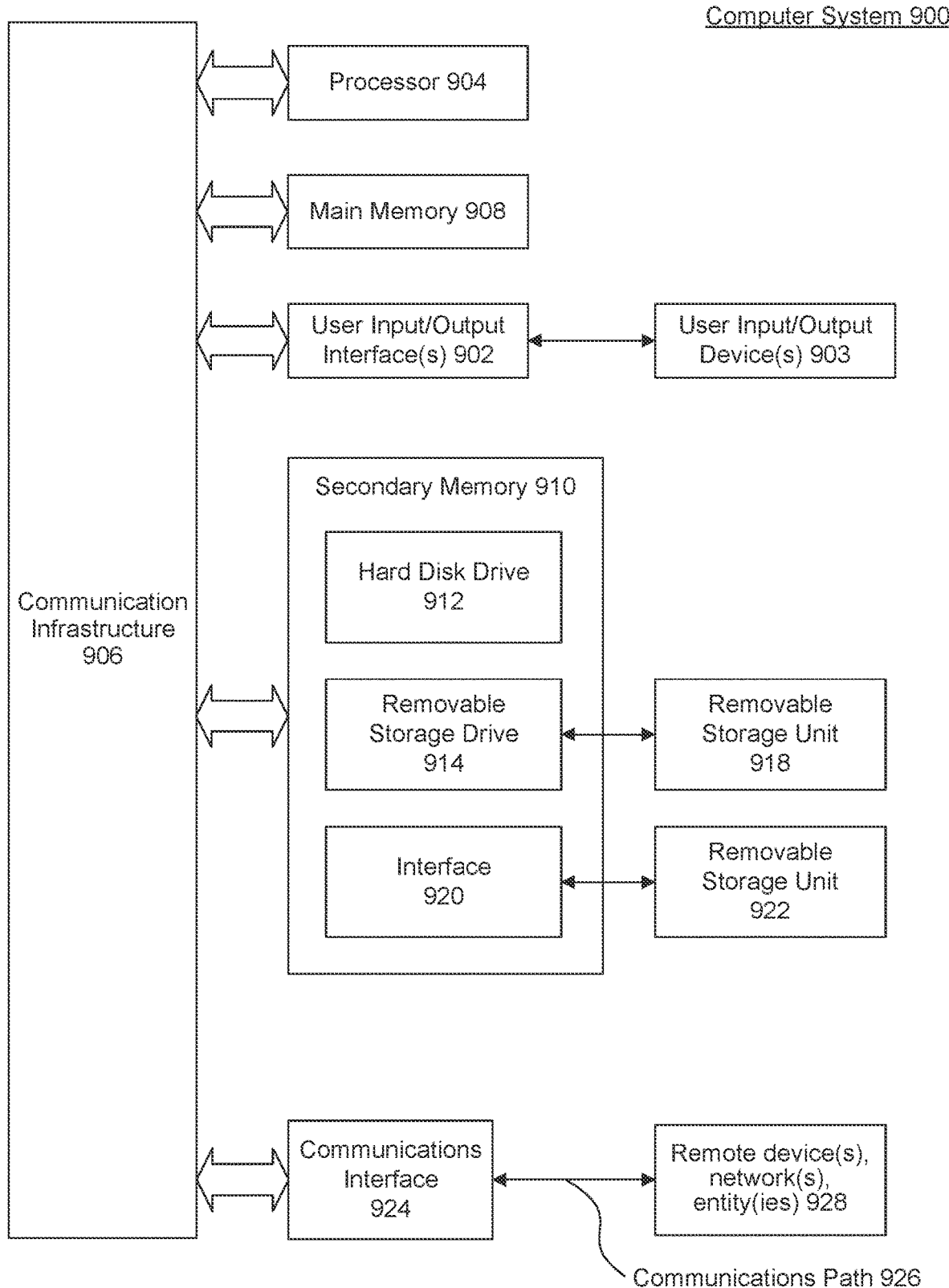
FIG. 9 illustrates an example computer system useful for implementing various embodiments.

Various embodiments and/or components therein can be implemented, for example, using one or more computer systems, such as computer system 900 shown in FIG. 9. Computer system 900 can be any computer or computing device capable of performing the functions described herein.

For example, one or more computer systems 900 can be used to implement any embodiments, and/or any combination or sub-combination thereof.

Computer system 900 includes one or more processors (also called central processing units, or CPUs), such as a processor 904. Processor 904 is connected to a communication infrastructure or bus 906. Computer system 900 may represent or comprise one or more systems on chip (SOC).

One or more processors 904 can each be a graphics processing unit (GPU). In some embodiments, a GPU is a processor that is a specialized electronic circuit designed to process mathematically intensive applications. The GPU can have a parallel structure that is efficient for parallel processing of large blocks of data, such as mathematically intensive data common to computer graphics applications, images, videos, etc.

Computer system 900 also includes user input/output device(s) 903, such as monitors, keyboards, pointing devices, etc., that communicate with communication infrastructure 906 through user input/output interface(s) 902.

Computer system 900 also includes a main or primary memory 908, such as random access memory (RAM). Main memory 908 can include one or more levels of cache. Main memory 908 has stored therein control logic (i.e., computer software) and/or data.

Computer system 900 can also include one or more secondary storage devices or memory 910. Secondary memory 910 can include, for example, a hard disk drive 912 and/or a removable storage device or drive 914. Removable storage drive 914 can be a floppy disk drive, a magnetic tape drive, a compact disk drive, an optical storage device, tape backup device, and/or any other storage device/drive.

Removable storage drive 914 can interact with a removable storage unit 918. Removable storage unit 918 includes a computer usable or readable storage device having stored thereon computer software (control logic) and/or data. Removable storage unit 918 can be a floppy disk, magnetic tape, compact disk, DVD, optical storage disk, memory card, and/any other computer data storage device. Removable storage drive 914 reads from and/or writes to removable storage unit 918 in a well-known manner.

According to an exemplary embodiment, secondary memory 910 can include other means, instrumentalities or other approaches for allowing computer programs and/or other instructions and/or data to be accessed by computer system 900. Such means, instrumentalities or other approaches can include, for example, a removable storage unit 922 and an interface 920. Examples of the removable storage unit 922 and the interface 920 can include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 900 can further include a communication or network interface 924. Communication interface 924 enables computer system 900 to communicate and interact with any combination of remote devices, remote networks, remote entities, etc. (individually and collectively referenced by reference number 928). For example, communication interface 924 can allow computer system 900 to communicate with remote devices 928 over communications path 926, which can be wired and/or wireless, and which can include any combination of LANs, WANs, the Internet, etc. Control logic and/or data can be transmitted to and from computer system 900 via communication path 926.

In some embodiments, a tangible apparatus or article of manufacture comprising a tangible computer useable or readable medium having control logic (software) stored thereon is also referred to herein as a computer program product or program storage device. This includes, but is not limited to, computer system 900, main memory 908, secondary memory 910, and removable storage units 918 and 922, as well as tangible articles of manufacture embodying any combination of the foregoing. Such control logic, when executed by one or more data processing devices (such as computer system 900), causes such data processing devices to operate as described herein.

Based on the teachings contained in this disclosure, it will be apparent to persons skilled in the relevant art(s) how to make and use embodiments of this disclosure using data processing devices, computer systems and/or computer architectures other than that shown in FIG. 9. In particular, embodiments can operate with software, hardware, and/or operating system implementations other than those described herein.

It is to be appreciated that the Detailed Description section, and not the Summary and Abstract sections, is intended to be used to interpret the claims. The Summary and Abstract sections can set forth one or more but not all exemplary embodiments as contemplated by the inventors, and thus, are not intended to limit this disclosure or the appended claims in any way.

While this disclosure describes exemplary embodiments for exemplary fields and applications, it should be understood that the disclosure is not limited thereto. Other embodiments and modifications thereto are possible, and are within the scope and spirit of this disclosure. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments can perform functional blocks, steps, operations, methods, etc. using orderings different than those described herein.

References herein to "one embodiment," "an embodiment," "an example embodiment," or similar phrases, indicate that the embodiment described can include a particular feature, structure, or characteristic, but every embodiment can not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein. Additionally, some embodiments can be described using the expression "coupled" and "connected" along with their derivatives. These terms are not necessarily intended as synonyms for each other. For example, some embodiments can be described using the terms "connected" and/or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described exemplary embodiments, but should be defined only in accordance with the following claims and their equivalents.

What is claimed is:

1. A method comprising:
   identifying a first hash map and a second hash map, wherein the first hash map comprises a first set of index values corresponding to a first set of data values and a first set of hash values corresponding to the first set of data values, and wherein the second hash map includes a second set of index values corresponding to a second set of data values and a second set of hash values corresponding to the second set of data values;
   comparing a first hash value from the first hash map, with a lowest index value of the first set of index values, with a second hash value from the second hash map, with a lowest index value of the second set of index values;
   identifying a lowest hash value between the first hash value and the second hash value based on the comparison;
   storing the lowest hash value and its corresponding index value and data value in a combined hash map;
   repeating the comparing, identifying the lowest hash value, and storing for both the first set of hash values and the second set of hash values, until all of the hash values from both the first set of hash values and the second set of hash values are stored in the combined hash map;
   receiving a query comprising one of a query data value or a query index value; and
   returning a result to the query, wherein the query was processed based on the combined hash map.

2. The method of claim 1, further comprising:
   moving the combined hash map from a memory storage to a disk storage.

3. The method of claim 2, wherein the combined hash map as stored on the disk storage includes an index value column and a data value column.

4. The method of claim 3, wherein the hash values are stored in metadata.

5. The method of claim 1, wherein the second set of index values is contiguous with the first set of index values.

6. The method of claim 1, wherein the first and second hash maps are stored on a disk storage, and wherein the storing comprises moving the value from the disk storage to a memory storage.

7. The method of claim 1, wherein the first set of index values and the second set of index values are maintained in the combined hash map.

8. A system comprising at least one processor, the at least one processor configured to perform operations comprising:
   identifying a first hash map and a second hash map, wherein the first hash map comprises a first set of index values corresponding to a first set of data values and a first set of hash values corresponding to the first set of data values, and wherein the second hash map includes a second set of index values corresponding to a second set of data values and a second set of hash values corresponding to the second set of data values;
   comparing a first hash value from the first hash map, with a lowest index value of the first set of index values, with a second hash value from the second hash map, with a lowest index value of the second set of index values;

identifying a lowest hash value between the first hash value and the second hash value based on the comparison;

storing the lowest hash value and its corresponding index value and data value in a combined hash map;

repeating the comparing, identifying the lowest hash value, and storing for both the first set of hash values and the second set of hash values, until all of the hash values from both the first set of hash values and the second set of hash values are stored in the combined hash map;

receiving a query comprising one of a query data value or a query index value; and returning a result to the query, wherein the query was processed based on the combined hash map.

9. The system of claim 8, the operations further comprising:

moving the combined hash map from a memory storage to a disk storage.

10. The system of claim 9, wherein the combined hash map as stored on the disk storage includes an index value column and a data value column.

11. The system of claim 10, wherein the hash values are stored in metadata.

12. The system of claim 8, wherein the second set of index values is contiguous with the first set of index values.

13. The system of claim 8, wherein the first and second hash maps are stored on a disk storage, and wherein the storing comprises moving the value from the disk storage to a memory storage.

14. The system of claim 8, wherein the first set of index values and the second set of index values are maintained in the combined hash map.

15. A non-transitory computer-readable medium having instructions stored thereon that, when executed by at least one computing device, cause the at least one computing device to perform operations comprising:

identifying a first hash map and a second hash map, wherein the first hash map comprises a first set of index values corresponding to a first set of data values and a first set of hash values corresponding to the first set of data values, and wherein the second hash map includes a second set of index values corresponding to a second set of data values and a second set of hash values corresponding to the second set of data values;

comparing a first hash value from the first hash map, with a lowest index value of the first set of index values, with a second hash value from the second hash map, with a lowest index value of the second set of index values;

identifying a lowest hash value between the first hash value and the second hash value based on the comparison;

storing the lowest hash value and its corresponding index value and data value in a combined hash map;

repeating the comparing, identifying the lowest hash value, and storing for both the first set of hash values and the second set of hash values, until all of the hash values from both the first set of hash values and the second set of hash values are stored in the combined hash map;

receiving a query comprising one of a query data value or a query index value; and returning a result to the query, wherein the query was processed based on the combined hash map.

16. The non-transitory computer-readable medium of claim 15, the operations further comprising:

moving the combined hash map from a memory storage to a disk storage.

17. The non-transitory computer-readable medium of claim 16, wherein the combined hash map as stored on the disk storage includes an index value column and a data value column.

18. The non-transitory computer-readable medium of claim 17, wherein the hash values are stored in metadata.

19. The non-transitory computer-readable medium of claim 15, wherein the second set of index values is contiguous with the first set of index values.

20. The non-transitory computer-readable medium of claim 15, wherein the first and second hash maps are stored on a disk storage, and wherein the storing comprises moving the value from the disk storage to a memory storage.

* * * * *